US012268614B2

(12) United States Patent
Dewey et al.

(10) Patent No.: US 12,268,614 B2
(45) Date of Patent: Apr. 8, 2025

(54) INTERBODY IMPLANT WITH ADJUSTING SHIMS

(71) Applicant: Warsaw Orthopedic, Inc., Warsaw, IN (US)

(72) Inventors: Jonathan M. Dewey, Memphis, TN (US); Richard A. Hynes, Melbourne Beach, FL (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 804 days.

(21) Appl. No.: 17/515,735

(22) Filed: Nov. 1, 2021

(65) Prior Publication Data

US 2022/0409389 A1 Dec. 29, 2022

Related U.S. Application Data

(63) Continuation-in-part of application No. 17/356,950, filed on Jun. 24, 2021, now Pat. No. 11,612,499.

(51) Int. Cl.
*A61F 2/44* (2006.01)
*A61F 2/30* (2006.01)

(52) U.S. Cl.
CPC .... *A61F 2/447* (2013.01); *A61F 2002/30433* (2013.01); *A61F 2002/30578* (2013.01); *A61F 2002/443* (2013.01)

(58) Field of Classification Search
CPC .. A61F 2/447; A61F 2/44; A61F 2/442; A61F 2/4461; A61F 2002/30433; A61F 2002/30578; A61F 2002/443

(Continued)

(56) References Cited

U.S. PATENT DOCUMENTS 4,401,112 A  8/1983 Rezaian
4,553,273 A  11/1985 Wu
(Continued)

FOREIGN PATENT DOCUMENTS

DE  44 16 605 C1  6/1995
EP  0 767 636 A1  4/1997
(Continued)

OTHER PUBLICATIONS

International Search Report, and Written Opinion for Application. No. PCT/US2019/019067, dated Jun. 3, 2019.
(Continued)

*Primary Examiner* — Jessica Weiss
(74) *Attorney, Agent, or Firm* — FOX ROTHSCHILD LLP

(57) ABSTRACT

An expandable implant may include a superior endplate and an inferior endplate hingedly coupled together. The superior endplate may have at least one track extending in a proximal-to-distal direction and an inferior endplate may have at least one track extending in the proximal-to-distal direction. The implant may further include a proximal plate having a superior engagement surface and an inferior engagement surface. At least one shim may be disposed within the at least one tracks of the superior endplate and interior endplate, and the at least one shim may define an angle of inclination between the superior endplate and interior endplate. The at least one shim may be insert between the superior and inferior endplates to effectuate expansion and angulation. In various embodiments, the superior endplate may be supported by the superior engagement surface and the inferior endplate may be supported by inferior engagement surface.

20 Claims, 16 Drawing Sheets

(58) Field of Classification Search
USPC .......................................... 623/17.11–17.16
See application file for complete search history.

(56) References Cited

U.S. PATENT DOCUMENTS

| | | | |
|---|---|---|---|
| 4,636,217 A | 1/1987 | Ogilvie et al. | |
| 4,759,769 A | 7/1988 | Hedman et al. | |
| 5,059,193 A | 10/1991 | Kuslich | |
| 5,171,278 A | 12/1992 | Pisharodi | |
| 5,336,223 A | 8/1994 | Rogers | |
| 5,390,683 A | 2/1995 | Pisharodi | |
| 5,522,899 A | 6/1996 | Michelson | |
| 5,554,191 A | 9/1996 | Lahille et al. | |
| 5,575,790 A | 11/1996 | Chen et al. | |
| 5,609,635 A | 3/1997 | Michelson | |
| 5,653,762 A | 8/1997 | Pisharodi | |
| 5,658,336 A | 8/1997 | Pisharodi | |
| 5,665,122 A | 9/1997 | Kambin | |
| 5,693,100 A | 12/1997 | Pisharodi | |
| 5,697,977 A | 12/1997 | Pisharodi | |
| 5,702,391 A | 12/1997 | Lin | |
| 5,702,453 A | 12/1997 | Rabbe et al. | |
| 5,702,455 A | 12/1997 | Saggar | |
| 5,797,918 A | 8/1998 | McGuire et al. | |
| 5,800,550 A | 9/1998 | Sertich | |
| 5,865,848 A | 2/1999 | Baker | |
| 5,893,890 A * | 4/1999 | Pisharodi ............. | A61F 2/4611 606/247 |
| 5,931,777 A | 8/1999 | Sava | |
| 5,941,885 A | 8/1999 | Jackson | |
| 5,971,987 A | 10/1999 | Huxel et al. | |
| 5,980,522 A | 11/1999 | Koros et al. | |
| 6,045,579 A | 4/2000 | Hochshuler et al. | |
| 6,074,343 A | 6/2000 | Nathanson et al. | |
| 6,080,193 A | 6/2000 | Hochshuler et al. | |
| 6,099,531 A | 8/2000 | Bonutti | |
| 6,102,949 A | 8/2000 | Biedermann et al. | |
| 6,102,950 A * | 8/2000 | Vaccaro ............... | A61F 2/4637 606/247 |
| 6,106,557 A | 8/2000 | Robioneck et al. | |
| 6,113,638 A | 9/2000 | Williams et al. | |
| 6,117,174 A | 9/2000 | Nolan | |
| 6,132,465 A | 10/2000 | Ray et al. | |
| 6,159,211 A | 12/2000 | Boriani et al. | |
| 6,159,244 A | 12/2000 | Suddaby | |
| 6,176,882 B1 | 1/2001 | Biedermann et al. | |
| 6,179,873 B1 | 1/2001 | Zientek | |
| 6,179,874 B1 * | 1/2001 | Cauthen ............... | A61F 2/4425 623/17.14 |
| 6,190,414 B1 | 2/2001 | Young et al. | |
| 6,193,757 B1 | 2/2001 | Foley et al. | |
| 6,217,579 B1 | 4/2001 | Koros | |
| 6,245,108 B1 | 6/2001 | Biscup | |
| 6,309,421 B1 | 10/2001 | Pisharodi | |
| 6,342,074 B1 | 1/2002 | Simpson | |
| 6,371,989 B1 | 4/2002 | Chauvin et al. | |
| 6,395,031 B1 | 5/2002 | Foley et al. | |
| 6,423,063 B1 | 7/2002 | Bonutti | |
| 6,432,106 B1 | 8/2002 | Fraser | |
| 6,436,140 B1 | 8/2002 | Liu et al. | |
| 6,443,989 B1 | 9/2002 | Jackson | |
| 6,443,990 B1 | 9/2002 | Aebi et al. | |
| 6,454,806 B1 | 9/2002 | Cohen et al. | |
| 6,454,807 B1 | 9/2002 | Jackson | |
| 6,461,359 B1 | 10/2002 | Tribus et al. | |
| 6,491,724 B1 | 12/2002 | Ferree | |
| 6,520,991 B2 | 2/2003 | Huene | |
| 6,520,993 B2 | 2/2003 | James et al. | |
| 6,527,803 B1 | 3/2003 | Crozet et al. | |
| 6,562,074 B2 | 5/2003 | Gerbec et al. | |
| 6,576,016 B1 | 6/2003 | Hochshuler et al. | |
| 6,623,525 B2 | 9/2003 | Ralph et al. | |
| 6,629,998 B1 | 10/2003 | Lin | |
| 6,635,086 B2 | 10/2003 | Lin | |
| 6,648,917 B2 | 11/2003 | Gerbec et al. | |
| 6,676,703 B2 | 1/2004 | Biscup | |
| 6,685,742 B1 | 2/2004 | Jackson | |
| 6,723,126 B1 | 4/2004 | Berry | |
| 6,770,096 B2 | 8/2004 | Bolger et al. | |
| 6,773,460 B2 | 8/2004 | Jackson | |
| 6,821,298 B1 | 11/2004 | Jackson | |
| 6,835,206 B2 | 12/2004 | Jackson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,923,814 B1 | 8/2005 | Hildebrand et al. | |
| 6,926,737 B2 | 8/2005 | Jackson | |
| 6,953,477 B2 | 10/2005 | Berry | |
| 6,964,687 B1 | 11/2005 | Bernard et al. | |
| 6,974,480 B2 | 12/2005 | Messerli et al. | |
| 6,984,234 B2 | 1/2006 | Bray | |
| 7,112,222 B2 | 9/2006 | Fraser et al. | |
| 7,135,043 B2 | 11/2006 | Nakahara et al. | |
| 7,137,997 B2 | 11/2006 | Paul | |
| 7,172,627 B2 | 2/2007 | Fiere et al. | |
| 7,188,626 B2 | 3/2007 | Foley et al. | |
| 7,204,853 B2 | 4/2007 | Gordon et al. | |
| 7,232,464 B2 | 6/2007 | Mathieu et al. | |
| 7,238,203 B2 | 7/2007 | Bagga et al. | |
| 7,255,700 B2 | 8/2007 | Kaiser et al. | |
| 7,316,532 B2 | 1/2008 | Matthys-Mark | |
| 7,316,714 B2 | 1/2008 | Gordon et al. | |
| 7,407,483 B2 | 8/2008 | Perez-Cruet et al. | |
| 7,481,766 B2 | 1/2009 | Lee et al. | |
| 7,491,168 B2 | 2/2009 | Raymond et al. | |
| 7,537,565 B2 | 5/2009 | Bass | |
| 7,618,456 B2 | 11/2009 | Mathieu et al. | |
| 7,625,394 B2 | 12/2009 | Molz, IV et al. | |
| 7,655,046 B2 | 2/2010 | Dryer et al. | |
| 7,678,148 B2 | 3/2010 | Peterman | |
| 7,703,727 B2 | 4/2010 | Selness | |
| 7,708,778 B2 | 5/2010 | Gordon et al. | |
| 7,708,779 B2 | 5/2010 | Edie et al. | |
| 7,727,280 B2 | 6/2010 | McLuen | |
| 7,753,958 B2 | 7/2010 | Gordon et al. | |
| 7,780,594 B2 | 8/2010 | Hutton | |
| 7,806,932 B2 | 10/2010 | Webb et al. | |
| 7,815,682 B1 | 10/2010 | Peterson et al. | |
| 7,819,801 B2 | 10/2010 | Miles et al. | |
| 7,824,428 B2 | 11/2010 | Mikkonen et al. | |
| 7,828,849 B2 | 11/2010 | Lim | |
| 7,846,167 B2 | 12/2010 | Garcia et al. | |
| 7,846,207 B2 | 12/2010 | Lechmann et al. | |
| 7,850,731 B2 | 12/2010 | Brittan et al. | |
| 7,850,733 B2 | 12/2010 | Baynham et al. | |
| 7,862,616 B2 | 1/2011 | Lechmann et al. | |
| 7,875,076 B2 | 1/2011 | Mathieu et al. | |
| 7,892,173 B2 | 2/2011 | Miles et al. | |
| 7,909,869 B2 | 3/2011 | Gordon et al. | |
| 7,914,559 B2 | 3/2011 | Carls et al. | |
| 7,967,821 B2 | 6/2011 | Sicvol et al. | |
| 7,981,031 B2 | 7/2011 | Frasier et al. | |
| 8,016,836 B2 | 9/2011 | Corrao et al. | |
| 8,062,375 B2 | 11/2011 | Glerum et al. | |
| 8,105,382 B2 | 1/2012 | Olmos et al. | |
| 8,118,870 B2 | 2/2012 | Gordon et al. | |
| 8,118,871 B2 | 2/2012 | Gordon et al. | |
| 8,123,810 B2 | 2/2012 | Gordon et al. | |
| 8,147,550 B2 | 4/2012 | Gordon et al. | |
| 8,172,903 B2 | 5/2012 | Gordon et al. | |
| 8,182,539 B2 | 5/2012 | Tyber et al. | |
| 8,257,442 B2 | 9/2012 | Edie et al. | |
| 8,262,570 B2 | 9/2012 | White et al. | |
| 8,262,662 B2 | 9/2012 | Beardsley et al. | |
| 8,287,597 B1 | 10/2012 | Pimenta et al. | |
| 8,303,498 B2 | 11/2012 | Miles et al. | |
| 8,303,658 B2 | 11/2012 | Peterman | |
| 8,303,663 B2 | 11/2012 | Jimenez et al. | |
| 8,317,866 B2 | 11/2012 | Palmatier et al. | |
| 8,323,185 B2 | 12/2012 | Perez-Cruet et al. | |
| 8,328,872 B2 | 12/2012 | Duffield et al. | |
| 8,343,048 B2 | 1/2013 | Warren, Jr. | |
| 8,353,826 B2 | 1/2013 | Weiman | |
| 8,355,780 B2 | 1/2013 | Miles et al. | |

(56) References Cited

U.S. PATENT DOCUMENTS

| | | |
|---|---|---|
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Amin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |

(56) References Cited

U.S. PATENT DOCUMENTS

| | | |
|---|---|---|
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Arnin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 * | 3/2018 | Fessler .................. A61F 2/447 |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |

(56) References Cited

U.S. PATENT DOCUMENTS

| | | |
|---|---|---|
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,172,515 B2 | 7/2019 | Lee et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,631 B2 * | 10/2019 | Williams .................. A61F 2/447 |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,523 B2 | 12/2020 | Weiman et al. |
| 10,874,524 B2 | 12/2020 | Bjork |
| 10,925,656 B2 | 2/2021 | Cole et al. |
| 10,959,855 B2 | 3/2021 | Miller et al. |
| 11,058,469 B2 | 7/2021 | Mahajan et al. |
| 11,147,680 B2 | 10/2021 | Tyber et al. |
| 11,179,234 B2 | 11/2021 | Dacosta et al. |
| 11,717,421 B2 * | 8/2023 | Laurence ............... A61F 2/4465 |
| | | 623/17.16 |
| 11,850,163 B2 * | 12/2023 | Dewey .................. A61F 2/4455 |
| 2002/0045943 A1 | 4/2002 | Uk |
| 2002/0045945 A1 | 4/2002 | Liu et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2003/0050701 A1 | 3/2003 | Michelson |
| 2003/0130739 A1 | 7/2003 | Gerbec et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2005/0209698 A1 * | 9/2005 | Gordon ................. A61F 2/4611 |
| | | 606/247 |
| 2006/0122701 A1 | 6/2006 | Kiester |
| 2006/0129244 A1 * | 6/2006 | Ensign .................. A61F 2/4455 |
| | | 623/17.16 |
| 2007/0218750 A1 | 9/2007 | Corrao et al. |
| 2007/0270859 A1 | 11/2007 | Companioni et al. |
| 2008/0132959 A1 | 6/2008 | Mikkonen et al. |
| 2009/0024158 A1 | 1/2009 | Viker |
| 2009/0292361 A1 | 11/2009 | Lopez |

(56) References Cited

U.S. PATENT DOCUMENTS

| | | |
|---|---|---|
| 2010/0082109 A1 | 4/2010 | Greenhalgh et al. |
| 2010/0191336 A1 | 7/2010 | Greenhalgh |
| 2010/0211176 A1 | 8/2010 | Greenhalgh |
| 2011/0118843 A1 | 5/2011 | Mathieu et al. |
| 2011/0130838 A1 | 6/2011 | Morgenstern Lopez |
| 2011/0153020 A1 | 6/2011 | Abdelgany et al. |
| 2011/0218572 A1 | 9/2011 | Lechmann et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215316 A1 | 8/2012 | Mohr et al. |
| 2013/0103153 A1 | 4/2013 | Blackwell et al. |
| 2013/0190876 A1 | 7/2013 | Drochner et al. |
| 2013/0226191 A1 | 8/2013 | Thoren et al. |
| 2013/0231747 A1 | 9/2013 | Olmos et al. |
| 2013/0304136 A1 | 11/2013 | Gourlaouen-Preissler et al. |
| 2013/0317312 A1 | 11/2013 | Eastlack et al. |
| 2014/0107790 A1 | 4/2014 | Combrowski |
| 2014/0114420 A1 | 4/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0277500 A1 | 9/2014 | Logan et al. |
| 2014/0303674 A1 | 10/2014 | Sasing |
| 2015/0223945 A1 | 8/2015 | Weiman et al. |
| 2015/0230931 A1 | 8/2015 | Greenhalgh |
| 2015/0238236 A1 | 8/2015 | Sasing |
| 2016/0008924 A1 | 1/2016 | Canourgues et al. |
| 2016/0022434 A1 | 1/2016 | Robinson |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0242930 A1 | 8/2016 | Duffield et al. |
| 2016/0256291 A1 | 9/2016 | Miller |
| 2016/0278830 A1 | 9/2016 | Arrington |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0231675 A1 | 8/2017 | Combrowski |
| 2017/0239062 A1* | 8/2017 | Williams ................ A61F 2/447 |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0116891 A1 | 5/2018 | Beale et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328540 A1 | 10/2019 | Seifert et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |

(56) References Cited

U.S. PATENT DOCUMENTS

| | | |
|---|---|---|
| 2020/0054461 A1 | 2/2020 | Marrocco et al. |
| 2020/0060844 A1 | 2/2020 | Mathieu et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0289287 A1 | 9/2020 | Emerick et al. |
| 2020/0297507 A1 | 9/2020 | Tott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0137701 A1 | 5/2021 | Miller et al. |
| 2021/0154811 A1 | 5/2021 | Spreiter et al. |
| 2021/0315707 A1 | 10/2021 | Keller et al. |
| 2021/0322179 A1* | 10/2021 | Miller .................. A61F 2/4455 |
| 2022/0015919 A1 | 1/2022 | Reah et al. |
| 2022/0133498 A1 | 5/2022 | Josse et al. |
| 2023/0372120 A1* | 11/2023 | Miller .................. A61F 2/447 |

FOREIGN PATENT DOCUMENTS

| | | |
|---|---|---|
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| FR | 2781998 A1 | 2/2000 |
| FR | 3082115 A1 | 12/2019 |
| GB | 2 377 387 A | 1/2003 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |
| WO | 2014/133755 A1 | 9/2014 |
| WO | 2017/168208 A1 | 10/2017 |
| WO | 2018049227 A1 | 3/2018 |

OTHER PUBLICATIONS

International Search Report and Written Opinion for Application No. PCT/US2019/019060, dated Jun. 5, 2019.

International Search Report and Written Opinion, PCT/IB2020/000932, Dated Jul. 29, 2021.

International Search Report and Written Opinion, PCT/IB2020/000942, Dated Aug. 10, 2021.

* cited by examiner

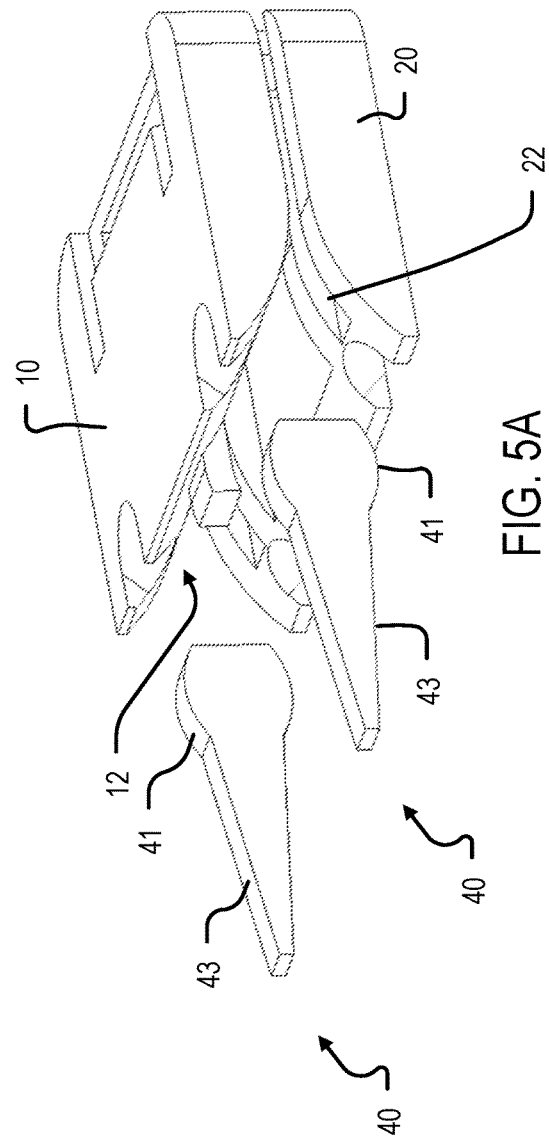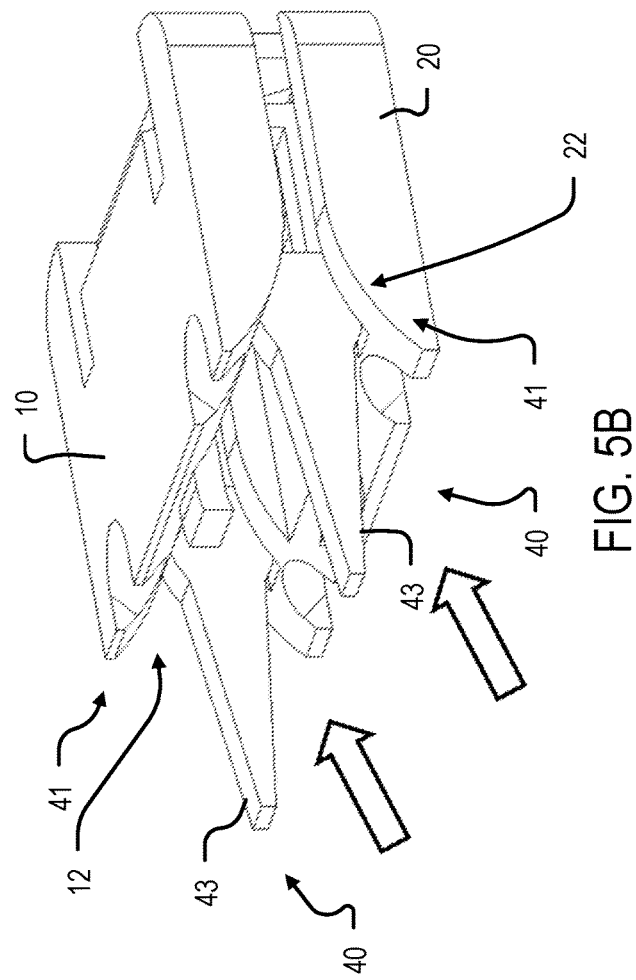
FIG. 5A
FIG. 5B

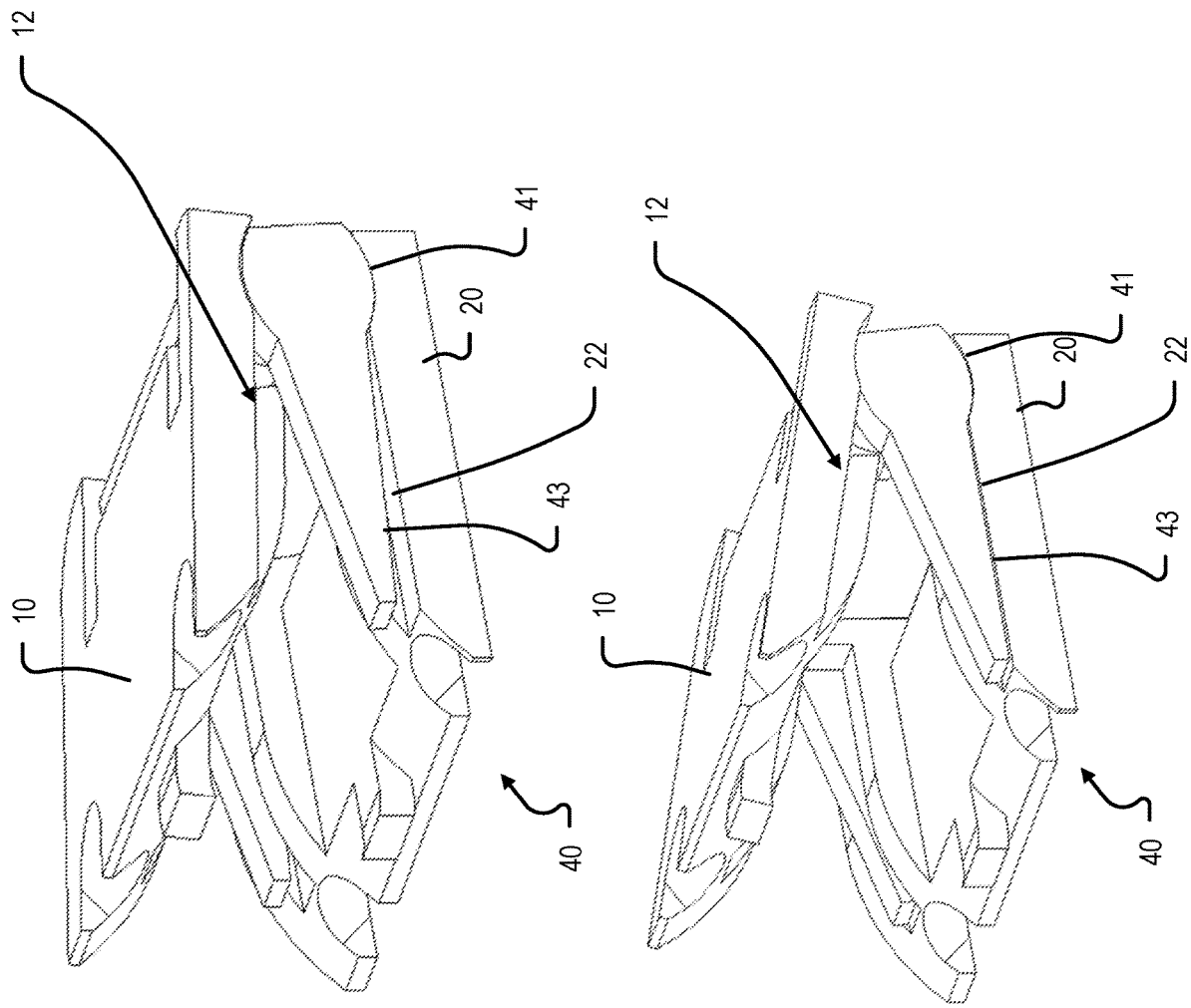

INTERBODY IMPLANT WITH ADJUSTING SHIMS

CROSS-REFERENCE TO RELATED APPLICATIONS

This application is a continuation in part of U.S. patent application Ser. No. 17/356,950, titled EXPANDABLE INTERBODY IMPLANT, and filed Jun. 24, 2021. The entire disclosure of which is incorporated herein by reference. This application also incorporates by reference the entire contents of U.S. application Ser. No. 17/307,578, titled EXTERNALLY DRIVEN EXPANDABLE INTERBODY AND RELATED METHODS, and filed May 5, 2021.

FIELD

The present technology is generally related to an expandable interbody implant for use in a medical procedure related to the spine. In some embodiments, disclosed implants may be used in an anterior cervical discectomy and fusion (ACDF) procedure although other uses in other areas of the spine or between two bones or bone portions are also contemplated.

BACKGROUND

Mechanically operated interbody implants may be used to align and/or realign a patient's spine during a medical procedure and/or for purposes of fusion, degenerative tissue and/or trauma/repair procedures. Conventional implants designed for the Thoracic and Lumbar region of the spine often include top and bottom endplates and a mechanical means to separate the top and bottom endplates. The mechanical mechanisms to separate the top and bottom endplates are often cumbersome and require a large footprint that is often unsuitable, for example, for ACDF type surgeries of the cervical portion of the spine. Additionally, these mechanical mechanisms may reduce available space in the interior of the implant which in turn may reduce the applicable volume for a fusion process.

SUMMARY

The techniques of this disclosure generally relate to an expandable interbody implant including a superior endplate and an inferior endplate hingedly coupled or combined together. The implant may include at least one shim for adjusting an expansion and/or lordosis of the implant.

In one aspect, the present disclosure provides for an expandable implant including a superior endplate and an inferior endplate hingedly coupled together. In various embodiments, the superior endplate may include a first distal surface supporting a first protrusion extending in a first lateral direction and a second protrusion extending in a second lateral direction opposite the first lateral direction, for example. In various embodiments, the superior endplate may include a third protrusion extending in a proximal direction away from a proximal surface of the superior endplate and the superior endplate may also have a first track and a second track extending in a proximal-to-distal direction, for example. In various embodiments, an inferior endplate may include a second distal surface supporting a first slot and a second slot, and the inferior endplate may have a fourth protrusion extending in a proximal direction away from a proximal surface of the inferior endplate, for example. In various embodiments, the inferior endplate may have a third track and a fourth track extending in the proximal-to-distal direction, for example. In various embodiments, the implant may include a proximal plate having a superior recess and an inferior recess disposed in a medial position of the proximal plate, for example. In various embodiments, the implant may include a first shim disposed within the first track and third track, and a second shim disposed within the second track and fourth track, for example. In various embodiments, the first protrusion may be mated within the first slot and the second protrusion may be mated within the second slot, for example.

In another aspect, the disclosure provides for an expandable implant. In various embodiments, the implant may include a superior endplate and an inferior endplate hingedly coupled together, for example. In various embodiments, the superior endplate may have at least one track extending in a proximal-to-distal direction on an interior surface thereof, for example. In various embodiments, an inferior endplate may have at least one track extending in the proximal-to-distal direction on an interior surface thereof, for example. In various embodiments, the implant may further include a proximal plate having a superior engagement surface and an inferior engagement surface, for example. Additionally, in various embodiments, at least one shim may be disposed within the at least one tracks of the superior endplate and interior endplate, and the at least one shim may define an angle of inclination between the superior endplate and interior endplate, for example. In various embodiments, the superior endplate may be supported by the superior engagement surface and the inferior endplate may be supported by inferior engagement surface, for example.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 5A is a perspective view showing the installation of a pair of shims.

FIG. 5B is a perspective view showing the installation of a pair of shims.

FIG. 8A is a perspective section view showing a completed installation of a pair of shims in a second position.

FIG. 8B is a perspective section view showing a completed installation of a pair of shims in a third position.

DETAILED DESCRIPTION

Figure 1:
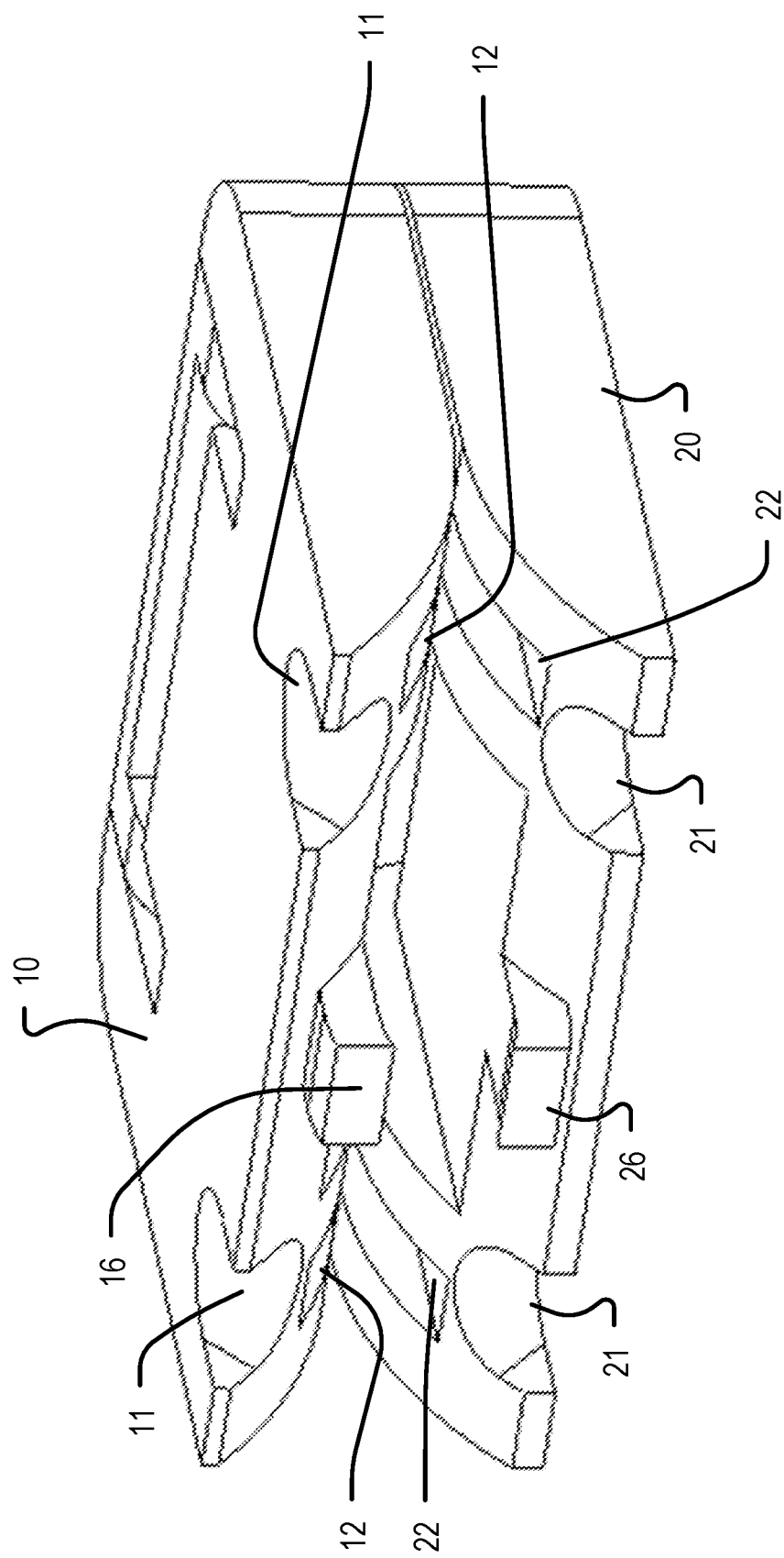
FIG. 1 is a perspective view of an expandable implant in a collapsed position.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-16 generally, various spinal implants 100 are disclosed. The components of spinal implant 100 can be fabricated from biologically acceptable materials suitable for medical applications, including metals, synthetic polymers, ceramics and bone material and/or their composites. For example, the components, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Figure 2:
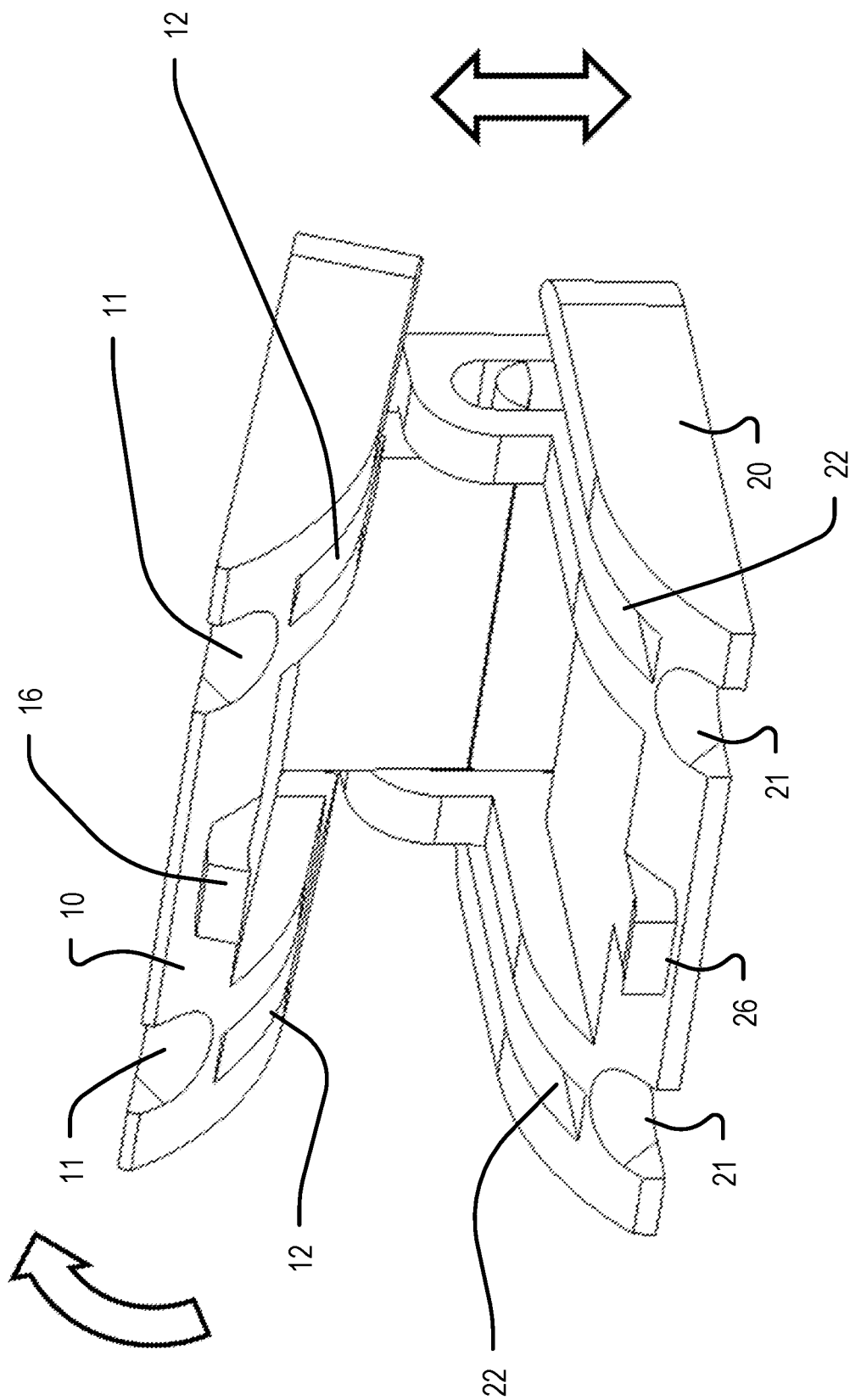
FIG. 2 is a perspective view of an expandable implant in an expanded position.

FIG. 1 is a perspective view of an expandable implant 100 in a collapsed position and FIG. 2 a perspective view of the expandable implant 100 in an expanded position. In the example embodiments, spinal implant 100 may include a superior endplate 10 and an inferior endplate 20, for example. The superior endplate 10 may include at least one bone screw cutout 11 (may also be referred to as a bone screw relief) and at least one track 12 (may also be referred to as a channel). Similarly, the inferior endplate 20 may include at least one bone screw cutout 21 (may also be referred to as a bone screw relief) and at least one track 22 (may also be referred to as a channel). Additionally, the proximal end 100P of implant 100 may include a first protrusion 16 and a second protrusion 26 extending in a proximal-to-distal direction, for example. In various embodiments, protrusion 16 may extend outward from superior endplate 10 and protrusion 26 may extend outward from inferior endplate 20 in a proximal direction. In other embodiments, protrusions 16, 26 may be bent over and/or curved upward and/or downward to intimately mate with proximal plate 30 (not illustrated). Protrusions 16, 26 may take any shape, e.g., rectangular, oval, dovetail, square, etc. Additionally, in some embodiments protrusions 16, 26 may be referred to as a locking or engagement protrusion and may be used to lock with and/or engage with a proximal plate 30 (see FIG. 4) which will be explained in detail below.

Figure 3:
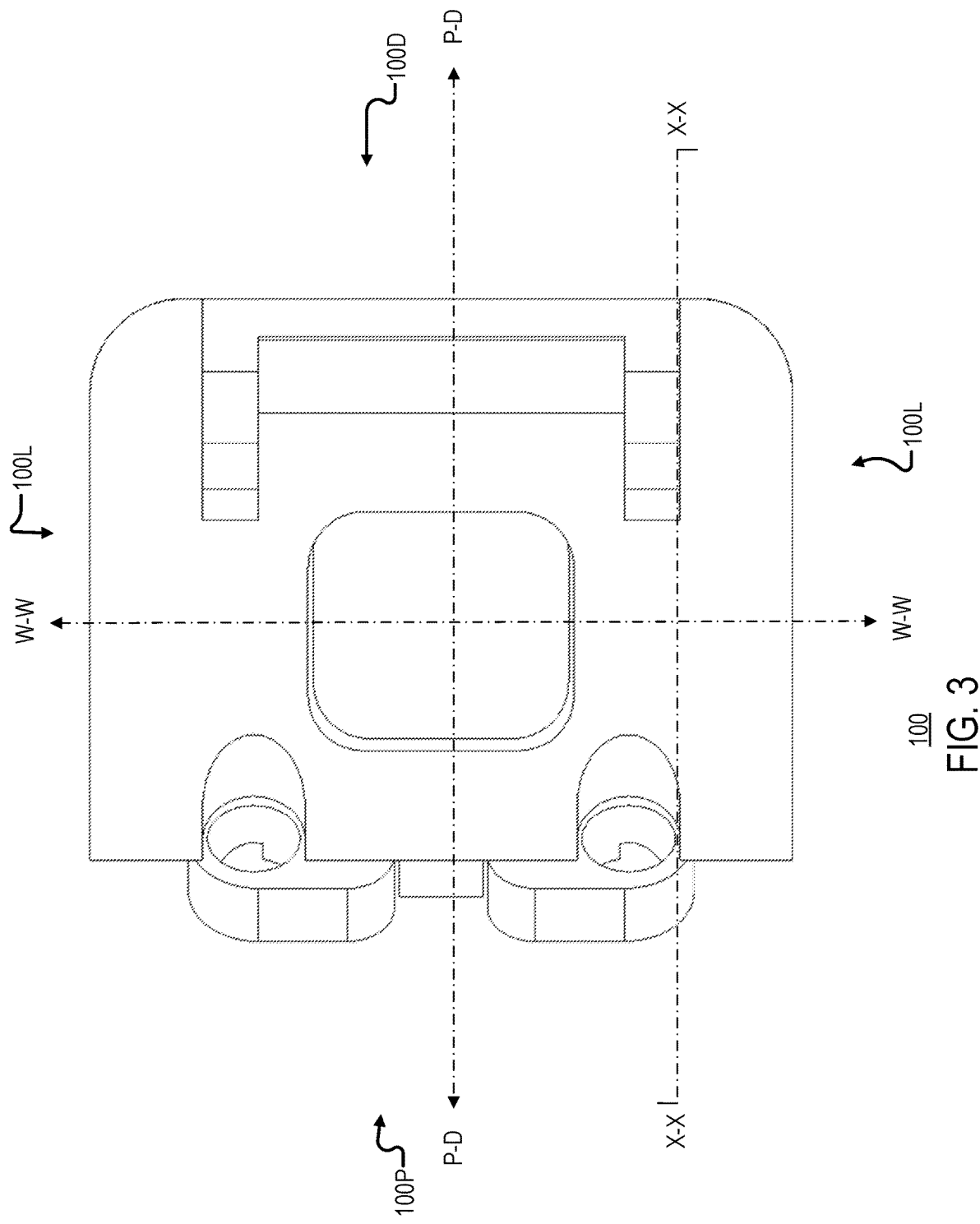
FIG. 3 is a plan view of an expandable implant showing various axes and section lines.

FIG. 3 is a plan view of the expandable implant 100 showing various axes and section lines. Implant 100 may extend in a proximal-to-distal direction along axis P-D from a proximal end 100P to a distal end 100D and may extend in a widthwise direction along axis W-W from a first lateral end 100L to a second lateral end 100L, for example. In various embodiments, the proximal-to-distal direction may refer to an insertion direction and the widthwise direction may be oriented in a perpendicular direction to the proximal-to-distal direction. In some embodiments, a distance from proximal end 100P to distal end 100D may be less than a distance from first lateral end 100L to second lateral end 100L. However, other embodiments may have alternate configurations in which a distance between lateral ends 100L is less than a distance between the proximal end 100P and distal end 100D. Section line X-X is taken through tracks 12, 22 of the superior endplate 10 and inferior endplate 20 and may correspond spatially to the perspective images shown in FIGS. 6-9. For example, the drawings shown in FIGS. 6-9 show a section cut through line X-X for ease of understanding the installation of shims 40, which will be explained in detail below.

Figure 4:
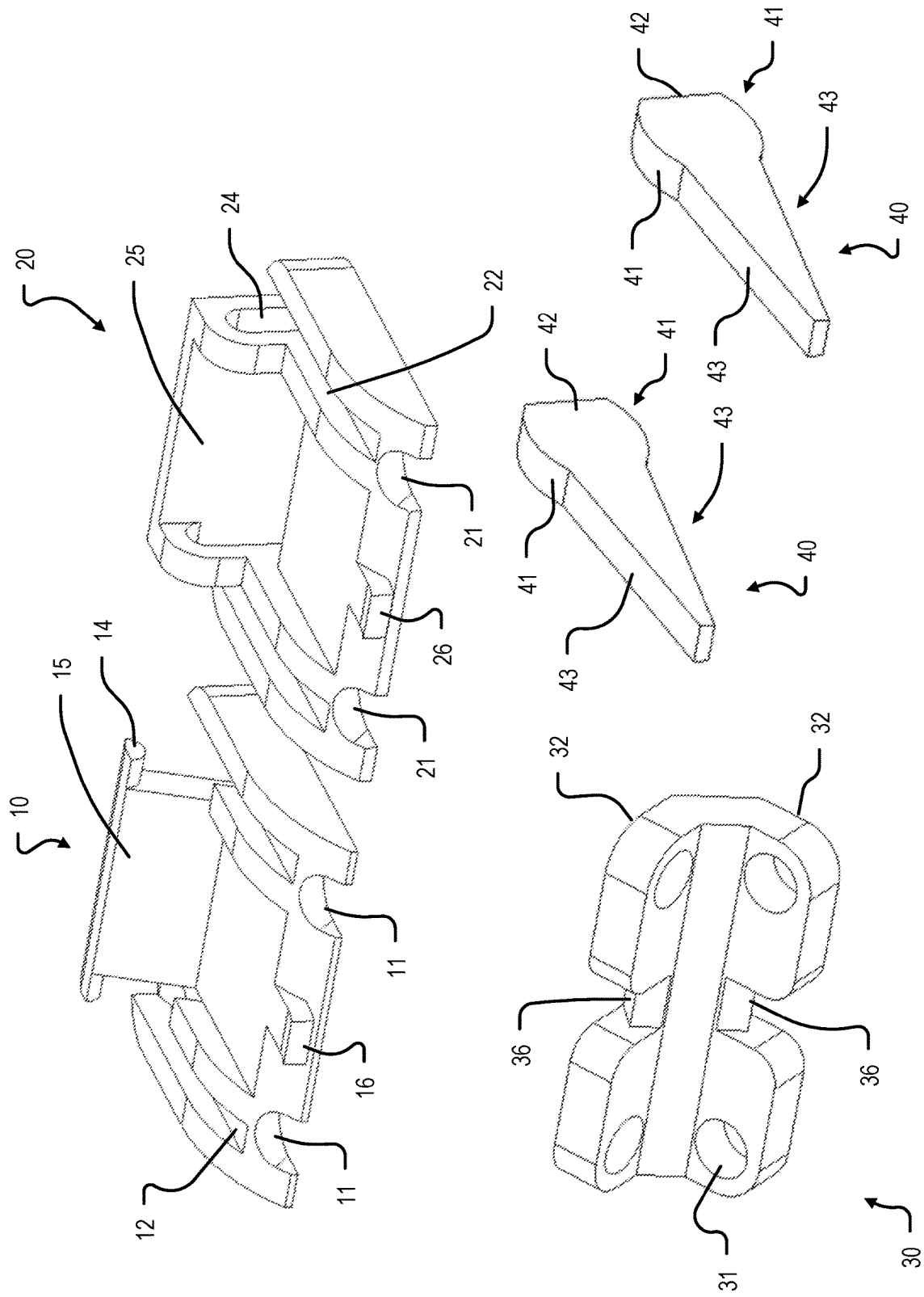
FIG. 4 is an exploded parts view of an expandable implant.

FIG. 4 illustrates an exploded parts view of various example components of implant 100. In the example embodiment, the interior of the superior endplate 10 and inferior endplate 20 are illustrated side by side for ease of understanding. In the example embodiment, superior endplate includes a first distal wall 15. In some embodiments, first distal wall 15 may be angled with respect to an outside surface of the superior endplate 10, for example. Additionally, first distal wall 15 may include a first lateral protrusion 14 that extends in a first lateral direction and a second lateral protrusion 14 that extends in a second lateral direction opposite the first lateral direction. In the example embodiment, lateral protrusions 14 include an arcuate surface and are generally shaped like a semi-circle, at least in a cross section view. Inferior endplate 20 may include a second distal wall 25. In some embodiments, second distal wall 25 may include a first slot 24 and a second slot 24 opposite the first slot. In various embodiments, the first and second lateral protrusions 14 may mate with and/or be inserted within and moveable within first and second slots 24 to hingedly couple the superior endplate 10 and the inferior endplate 20, for example. Additionally, when the superior endplate 10 and inferior endplate 20 are coupled together, the first distal wall 15 of the superior endplate 10 may be positioned more proximal than the second distal wall 25 of the inferior endplate and the superior endplate 10 and inferior endplate 20 may move with respect to one another as the first and second lateral protrusions 14 slide and/or move up and down within first and second slots 24, therefore allowing distraction of the disc space, while also allowing an angle of inclination between the superior endplate 10 and inferior endplate 20 to be adjusted, allowing lordosis or kyphosis of the disc space. The unconstrained nature of the coupling of the endplates allows any combination of movements between the endplates, such as a relatively substantial amount of lordosis coupled with slight distraction, full distraction and lordosis, etc.

Various implant 100 embodiments may include at least one shim 40 for expanding implant 100 and at least one proximal plate 30 for supporting and/or locking implant in an expanded configuration, for example. In some embodiments, proximal plate 30 may be referred to as an "anterior plate," e.g., depending on angle and/or technique of insertion into the human body. In the example embodiment, a first shim 40 and a second shim 40 may be positioned within tracks 12, 22, respectively, to expand implant 100. In some embodiments, a third shim 40 and a corresponding channel may be positioned in a medial position approximately equidistant from a first lateral shim 40 and a second lateral shim 40 (not illustrated). Each shim 40 may include a bulbous distal side or end having upper and lower curved surfaces 41 and a distal end surface 42. Additionally, each shim 40 may be widest at the distal side and gradually taper along planar surfaces 43 towards a proximal end thereof, for example. In various embodiments, proximal plate 30 may be generally "C" shaped or "U" shaped and include upper and lower bearing surfaces 32 that act against and support the superior endplate 10 and inferior endplate 20 at corresponding surfaces on the proximal side thereof, for example. Proximal plate 30 may include a first and second recess 36 with which protrusions 16 and 26 may nest inside of thereby also providing a bearing surface and constraining motion of proximal plate 30 in the lateral direction. In this way, the interior inclined surfaces of the superior endplate 10 and inferior endplate 20 may rest against bearing surfaces 32 and the protrusions 16, 26 may rest against and be confined within recesses 36. Additionally, proximal plate 30 may include at least one bone screw aperture 31 which may orient a bone screw 60 (see FIG. 13) in a target trajectory, for example.

Referring generally to FIGS. 5A-9, a method of installation of shims 40 will be disclosed. FIGS. 5A and 5B are perspective views showing the installation of a pair of shims 40. In the example embodiment, an end user such as a surgeon may insert a first shim 40 along track 12 of the superior endplate 10 and track 22 of the inferior endplate 20. In the example embodiment, the bulbous distal end may be inserted first such that curved surfaces 41 act against corresponding surfaces of tracks 12 and 22 thereby expanding a distance between the superior and inferior endplates 10, 20, for example. In various embodiments, a first shim 40 may be insert before a second shim 40, or alternatively, both the first shim 40 and second shim 40 may be insert at the same time. In some embodiments, a pair of shims 40 may be joined together by a crossbar (not illustrated) and inserted simultaneously. Shims 40 may be insert by forceps, pliers, and/or specialized gripping tools, for example. It shall be understood that an inserter base could be used for holding at least one of the superior endplate 10 and/or inferior endplate 20, and such an inserter could have a central track and shuttle. In some embodiments, the shuttle may be be used to grasp both shims 40 and hold them at the same Anterior—Posterior depth, such that during insertion they would insert at the same depth. The central track that the shuttle rides in may allow the shims 40 to be easily moved in the Anterior—Posterior direction. This would allow grasping of the endplates and shims for ease of insertion. The endplates may first be inserted in the collapsed condition. The shuttle may then be advanced along the track inserting the shims 40 between the endplates 10, 20 and ensuring the same depth.

Figure 6:
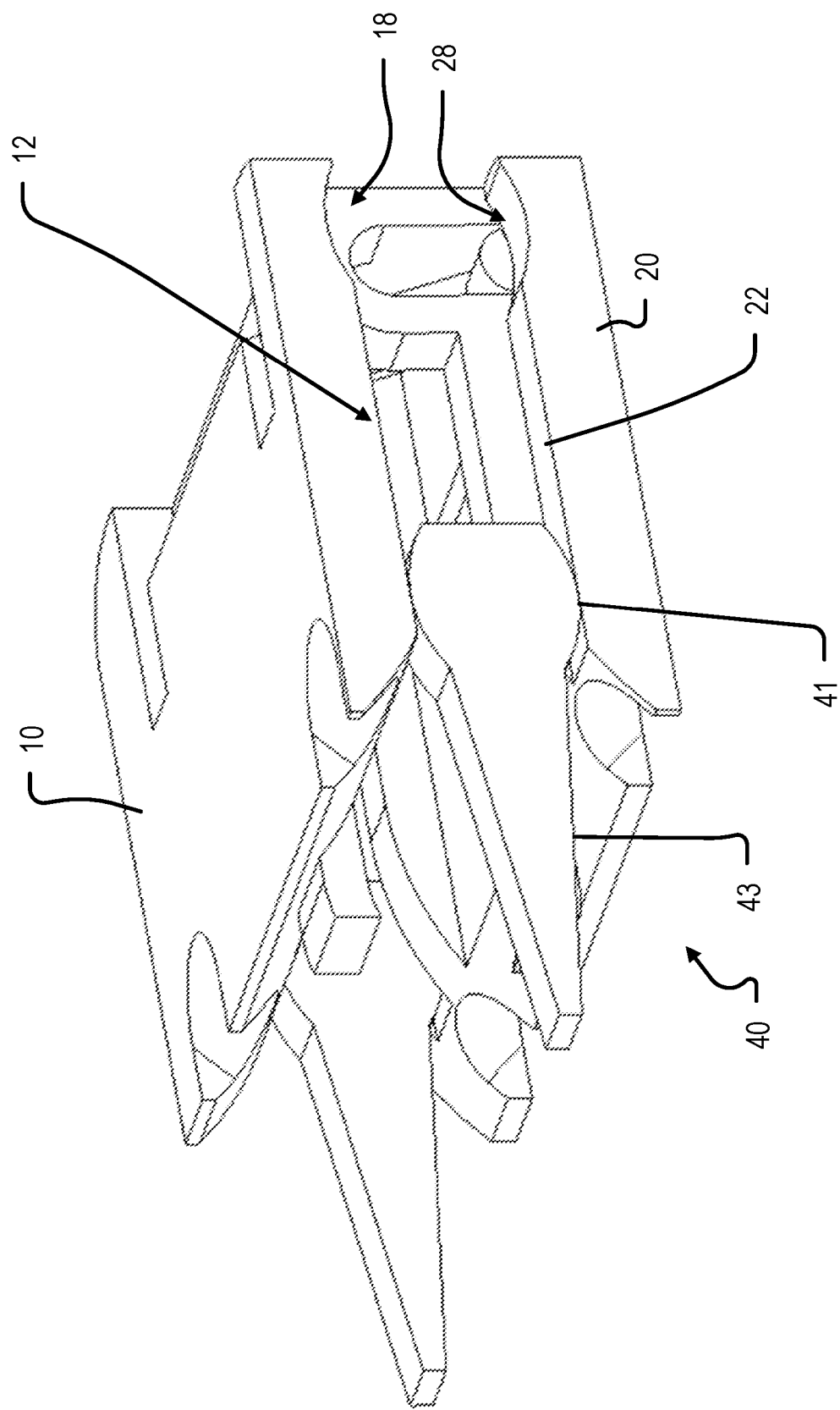
FIG. 6 is a perspective section view showing an installation step of a pair of shims.
Figure 7:
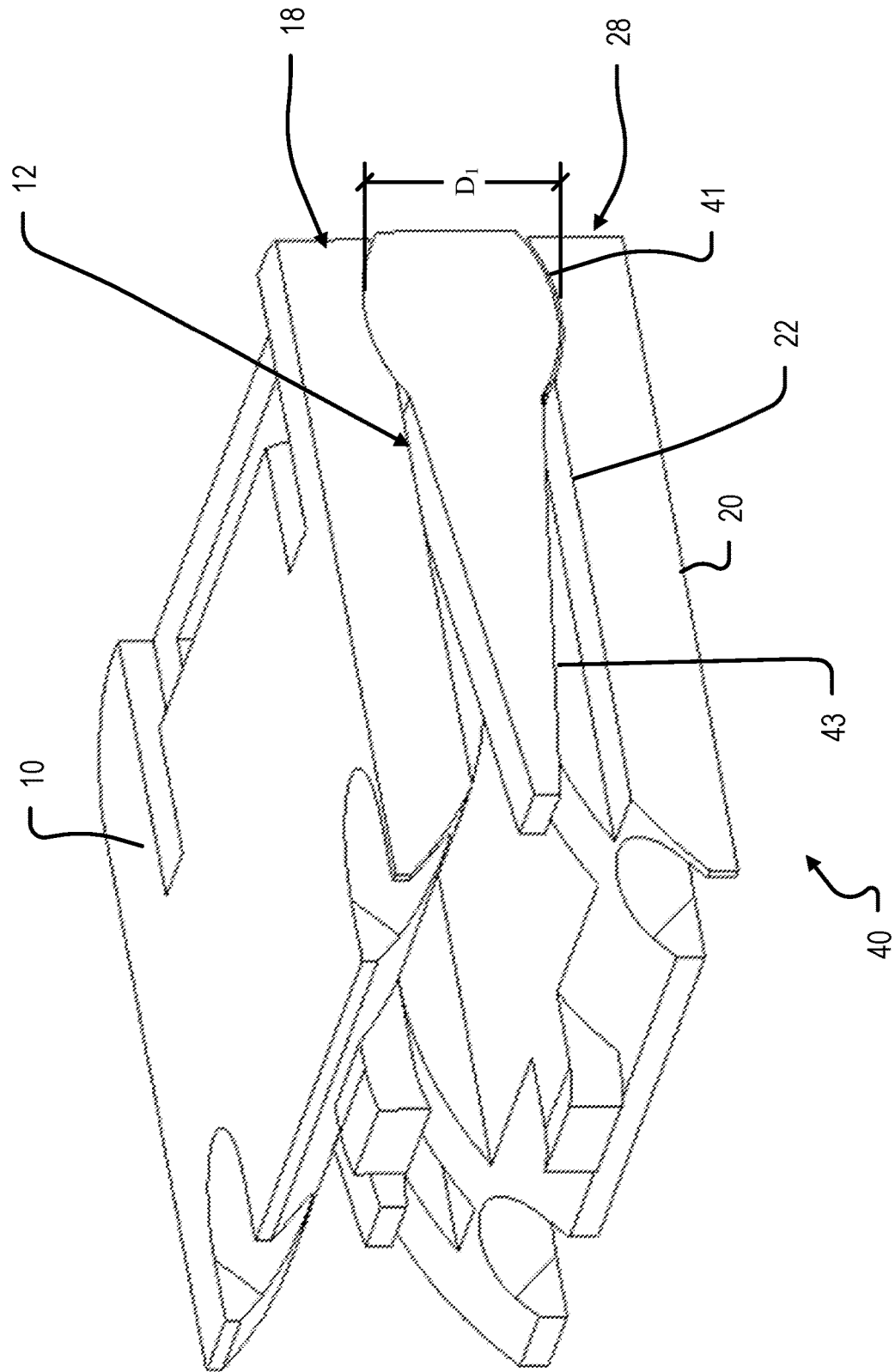
FIG. 7 is a perspective section view showing a completed installation of a pair of shims in a first position.

FIGS. 6 and 7 are perspective section views corresponding spatially to section cut X-X of FIG. 3 and show the installation of a pair of shims 40. In the example embodiment, it is shown that tracks 12, 22 each include a socket 18, 28 at the distal side of implant 100. In various embodiments, sockets 18, 28 may comprise a curved surface and/or arcuate shape generally corresponding to the bulbous end of shim 40, for example. Additionally, in various embodiments, sockets 18, 28 may be referred to as a curved recess. As shims 40 are inserted into corresponding tracks 12, 22, the superior endplate 10 and inferior endplate 20 may move relative to one another as first and second lateral protrusions 14 slide and/or move within first and second slots 24. FIG. 7 shows a completed installation of a pair of shims 40 in a first position where the bulbous ends of shims 40 are seated within corresponding sockets 18, 28. For example, curved surfaces 41 are in direct contact with the corresponding curved surfaces of sockets 18, 28 and the tapering surfaces 43 are positioned approximately midway between the superior endplate 10 and inferior endplate 20. In the example embodiment, a relative height of expansion may be defined by a height $D_1$ measured from a center of an upper curved surface 41 and a center of a lower curved surface 41 of shim 40, for example as shown in FIG. 7. In various embodiments, the curved surfaces 41 of shim 40 could also be faceted (along with the sockets 18, 28 they contact) to allow discrete stopping points and/or angulations. Additionally, in some embodiments the bulbous distal end mating into sockets 18, 28 may be reversed which may also encompass the shims being symmetric. Furthermore, in some embodiments the shims may include a distal end having a bulbous outward protrusion on one side and a concave inward void space on the other. The surface featuring of the tracks 12, 22 may include a corresponding geometry to accommodate shims 40.

FIGS. 8A and 8B are perspective section views corresponding spatially to section cut X-X of FIG. 3. In the example illustrations, implant 100 is expanded and lordosed. Similar to FIGS. 6 and 7, the bulbous ends of shims 40 are seated within corresponding sockets 18, 28 and the curved surfaces 41 are in direct contact with the corresponding curved surfaces of sockets 18, 28. In the example configuration of FIG. 8A, a lowermost tapering surface 43 is positioned just above track 22 and implant 100 is lordosed at a first angle of inclination. In the example configuration of FIG. 8B, a lowermost tapering surface 43 directly contacts track 22 and implant 100 is lordosed at a second angle of inclination greater than the first angle of inclination, for example. In this way, a maximum angle of inclination between endplates is defined by shims 40 and in a position where at least one of the tapering surfaces 43 directly contacts an adjacent track 12, 22.

Figure 9A:
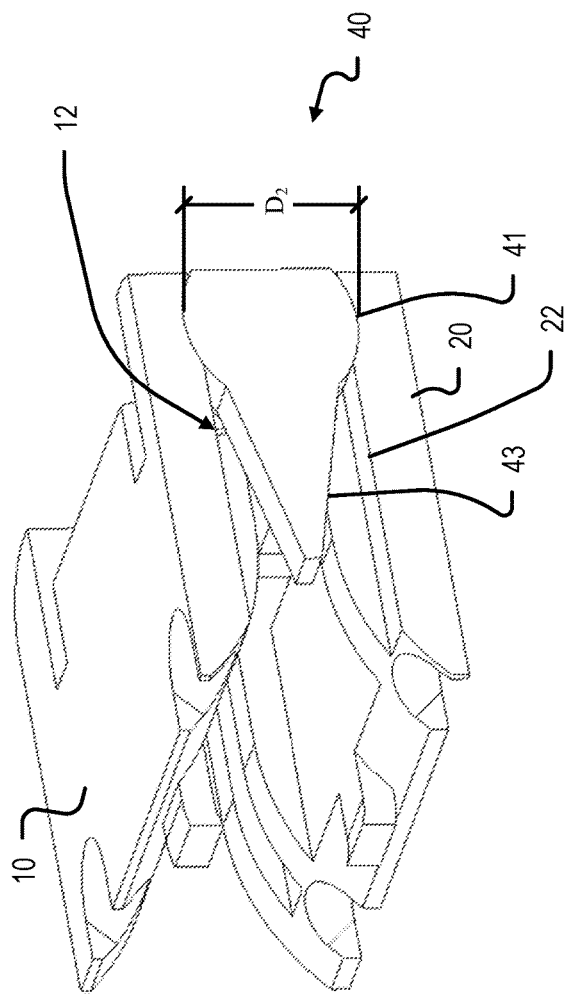
FIG. 9A is a perspective section view showing a completed installation of an alternate type of pair of shims in a second position.
Figure 9B:
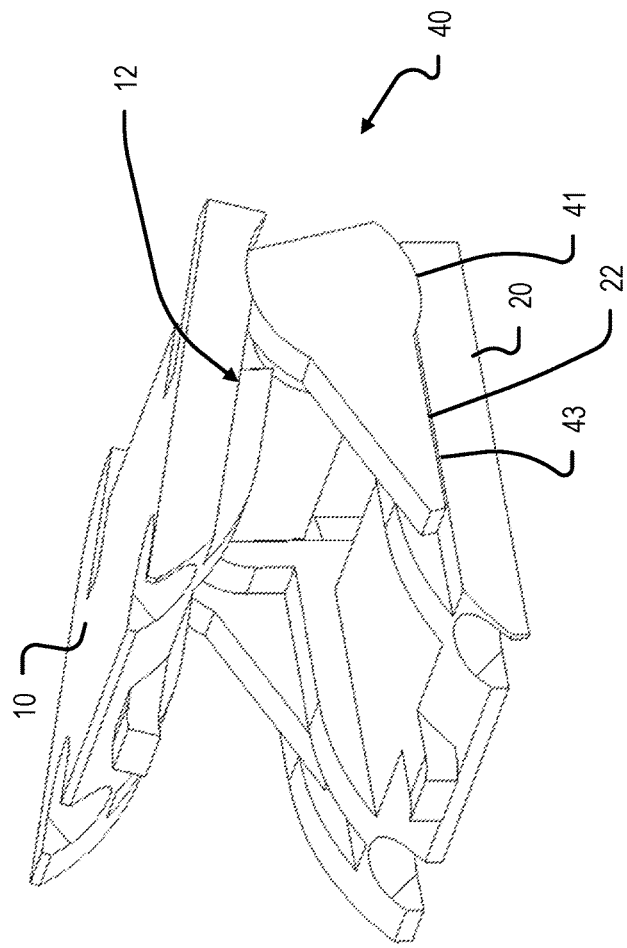
FIG. 9B is a perspective section view showing a completed installation of a pair of shims in a third position.

FIGS. 9A and 9B are perspective section views corresponding to section cut X-X of FIG. 3. The embodiment of FIGS. 9A and 9B functions in a substantially similar way as the embodiments of FIGS. 8A and 8B, for example. In the example illustrations, implant 100 is expanded via insertion of the shims 40 and lordosed. In some embodiments, implant 100 may be expanded by using an external expansion mechanism or distractors on the endplates 10, 20, or even driving the surrounding anatomy through the use of traction or rotation. In the example embodiment, a relatively larger shim 40 is utilized, e.g., a second type of shim 40 that is taller and/or wider than shims 40 of FIGS. 8A and 8B. In the example embodiment, the relatively wider shims 40 may be used to expand implant 100 by a relatively greater amount, for example. In the example embodiment, a relative height of expansion may be defined by a height $D_2$ measured from a center of an upper curved surface 41 and a center of a lower curved surface 41 of shim 40, for example as shown in FIG. 9A. It should be noted that in the case of conducting a coronal correction, a surgeon may optionally use a first shim 40 having a relatively shorter height (see FIGS. 8A-8B) and a second shim 40 having a relatively larger height (see FIGS. 9A-9B).

Figure 10:
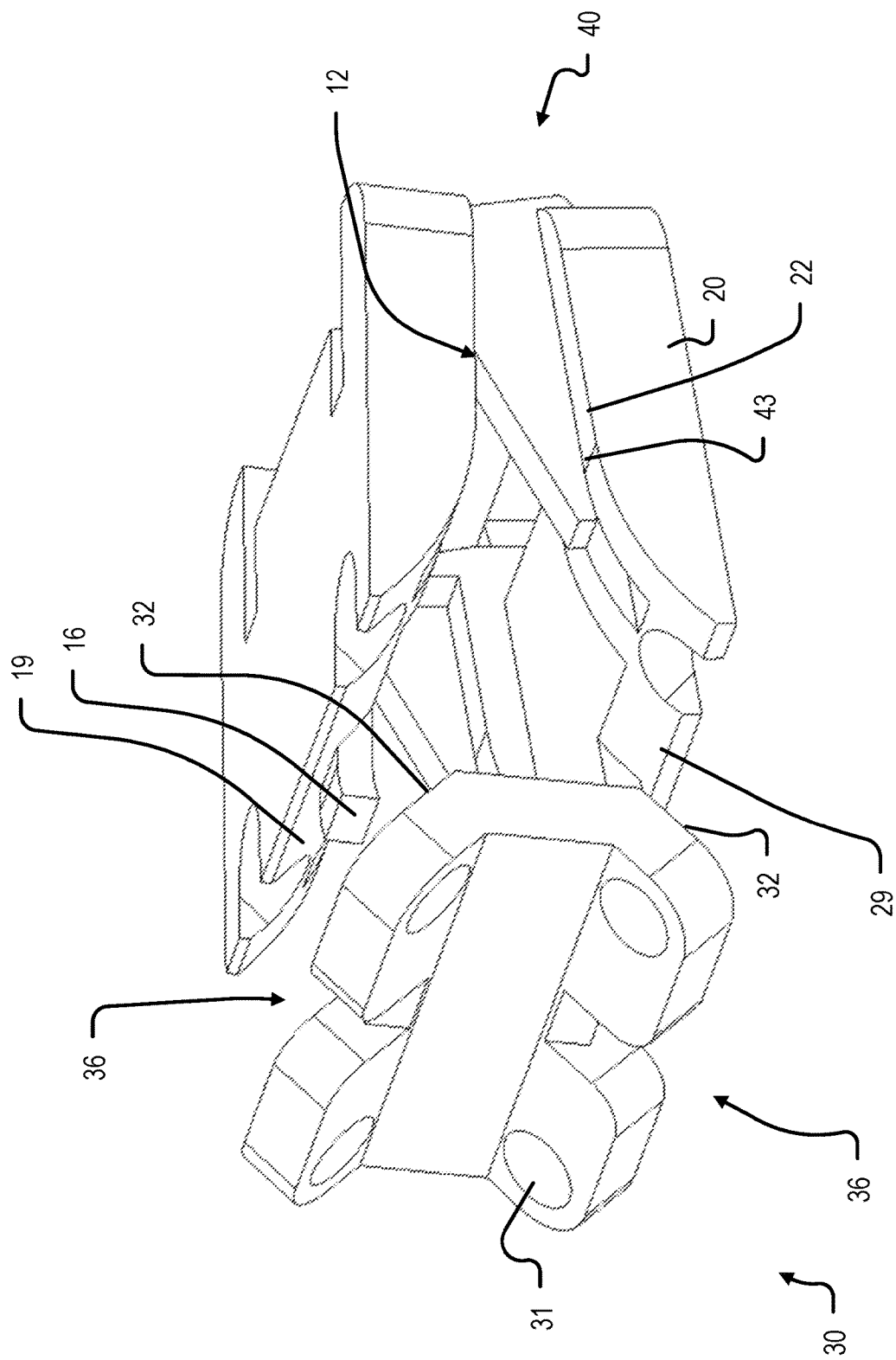
FIG. 10 is a perspective view showing an installation step of a proximal plate.
Figure 11:
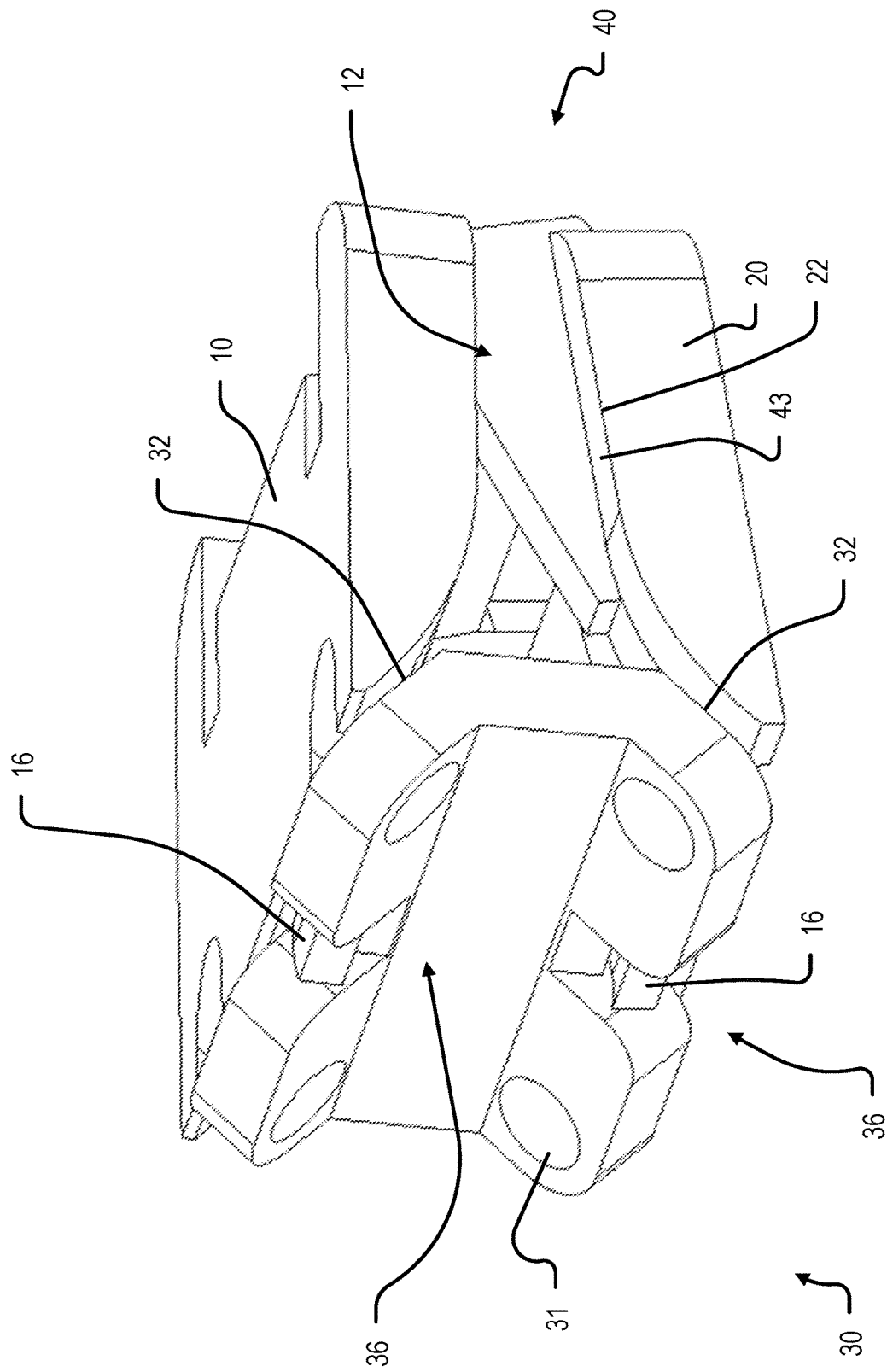
FIG. 11 is a perspective view showing an installation of a proximal plate.
Figure 12:
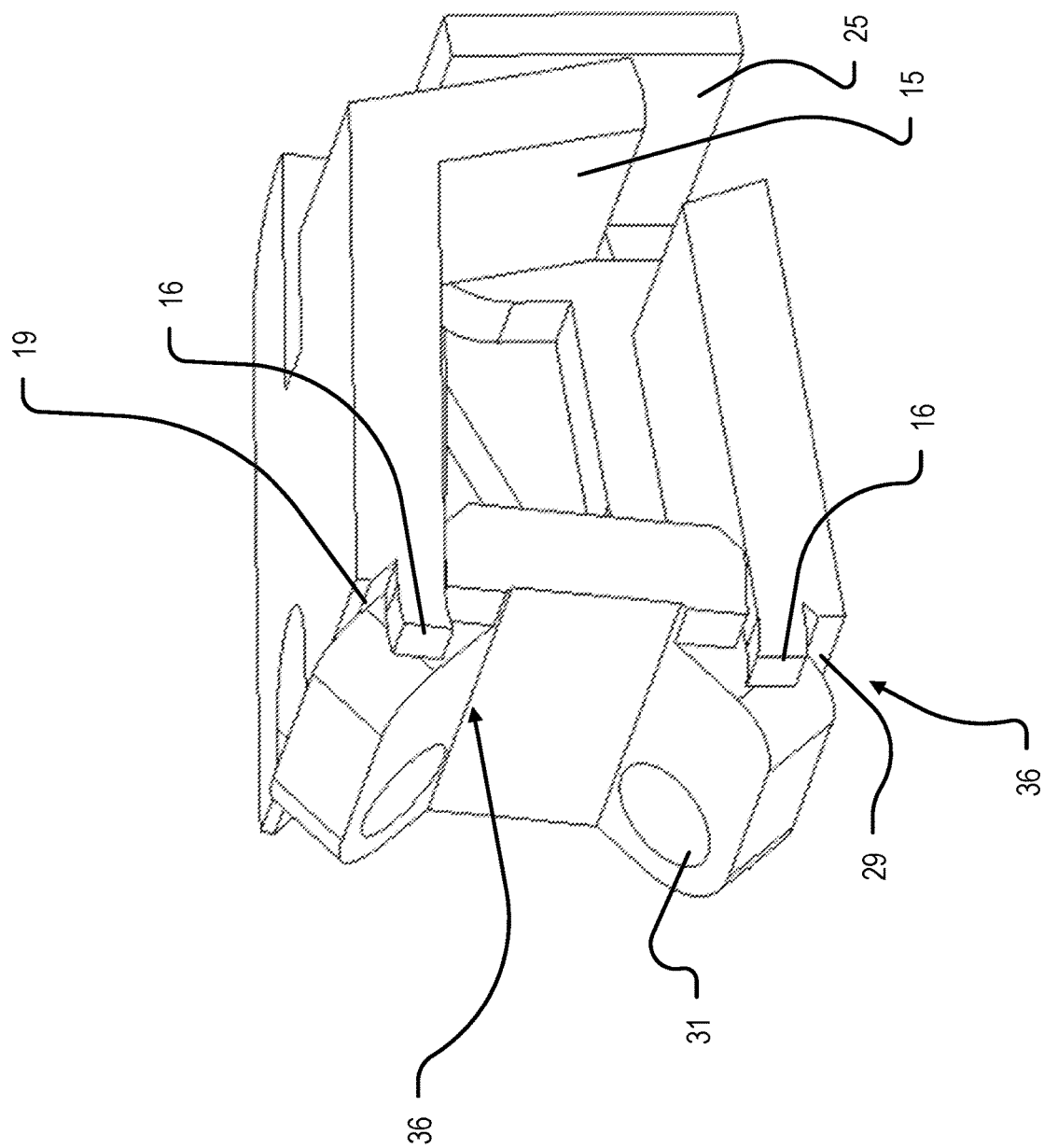
FIG. 12 is a sectioned perspective view of the embodiment of FIG. 11.

FIGS. 10 and 11 are perspective views showing an installation step of a proximal plate 30 and FIG. 12 is a sectioned perspective view of the embodiment of FIG. 11. In the example embodiment, both shims 40 are positioned between the superior and inferior endplates 10, 20 and the implant is expanded and lordosed to a desired configuration as explained previously. In the example embodiment, a proximal plate 30 is positioned against the superior and inferior endplates 10, 20 by nesting the protrusions 16 within corresponding recesses 36 of the proximal plate. Additionally, the proximal side or end of the superior endplate 10 includes an engagement surface 19 that directly contacts the upper bearing surface 32 and the proximal side or end of the inferior endplate 20 includes an engagement surface 29 that directly contacts the upper bearing surface 32. As protrusions 16 and 26 mate with slots 36 and as surfaces 19 and 29 bear on surfaces 32, the compressive force on the endplates 10, 20 may be supported through the endplates 10, 20 in the anterior direction and through the shims 40 posteriorly. Additionally, the compressive loads on the endplates 10, 20 through surfaces 19, 29 and 32 may urge and/or push the proximal plate 30 anteriorly, yet the curved geometry of protrusions 16 and 26 sitting in grooves 36 may retain the proximal plate 30 directly against the endplates.

For example, because surfaces 19 and 29 are curved, and surfaces 32 are planar and/or flat differently sized proximal plates 30 may be used in combination with different sets of shims 40 and still have the same, similar, and/or substantially the same load-bearing characteristics as described above. In one example, shorter height shims 40 may be used in combination with a shorter height proximal plate 30 to give less distraction and less lordosis. In another embodiment, the same short shims 40 may be used with a relatively taller proximal plate 30 to give less distraction with more lordosis. In still another example embodiment, taller shims 40 could be used with a relatively taller proximal plate 30 to create a construct that has more distraction, but less lordosis. In a broader sense, the shims 40 may define a posterior height and the proximal plate 30 may define an anterior height, such that the combination of shims 40 and proximal plate 30 may allow the surgeon to dial in the desired distraction and lordosis for a particular patient. The sockets 18, 28 on the endplates 10, 20 and the bulbous distal end of the shims 40 may coordinate the movement of the two endplates 10, 20 relative to each other. In some embodiments, lacking sockets 18, 28 and a bulbous distal end of the shims 40, the endplates 10, 20 may shift relative to each other. Therefore, embodiments in accordance with the principles of this disclosure contemplate the use of a variety of differently sized and angled proximal plates 30 and shims 40 than those examples specifically illustrated in the FIGS.

Figure 13:
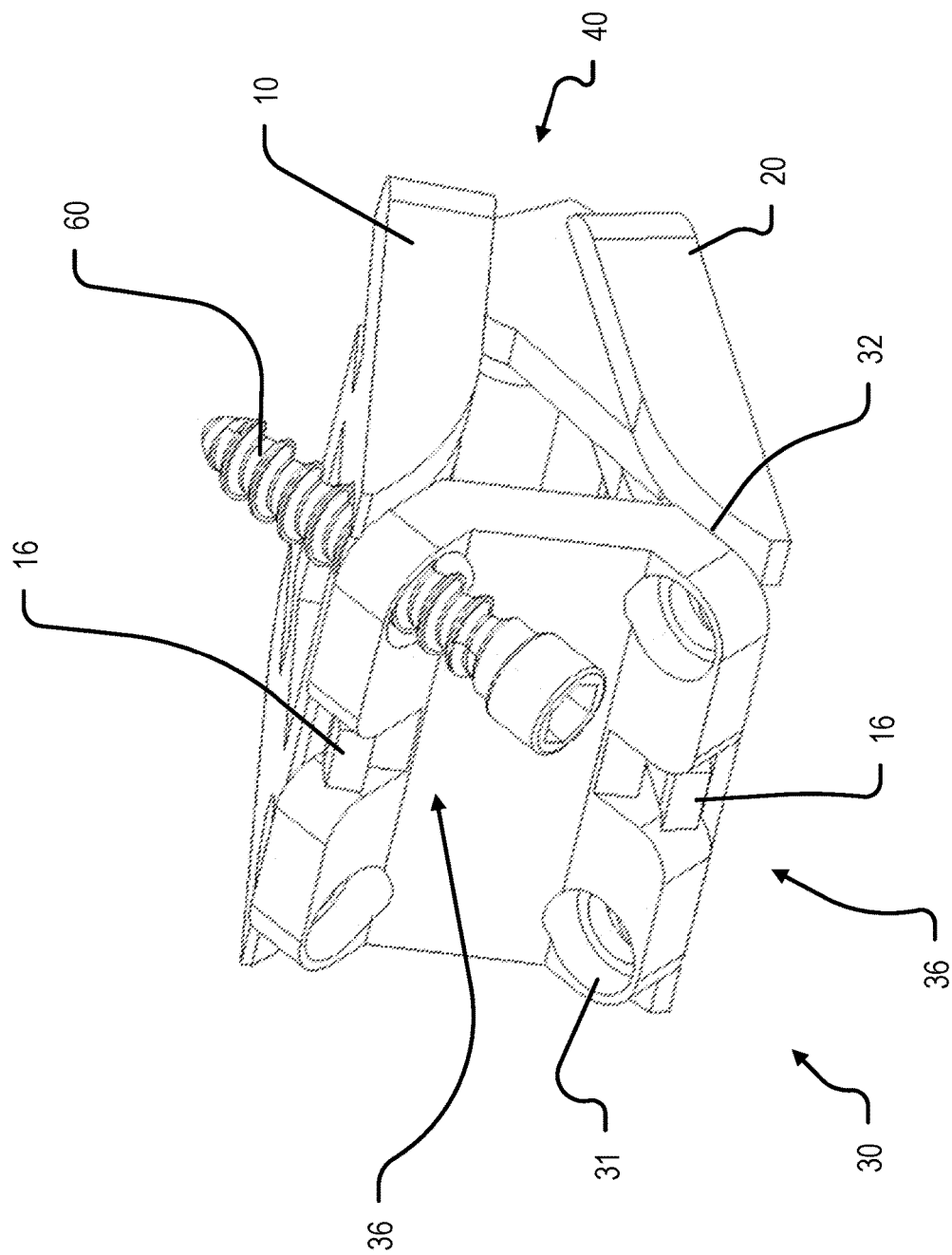
FIG. 13 is a perspective view showing an installation of a bone screw in a proximal plate.
Figure 14:
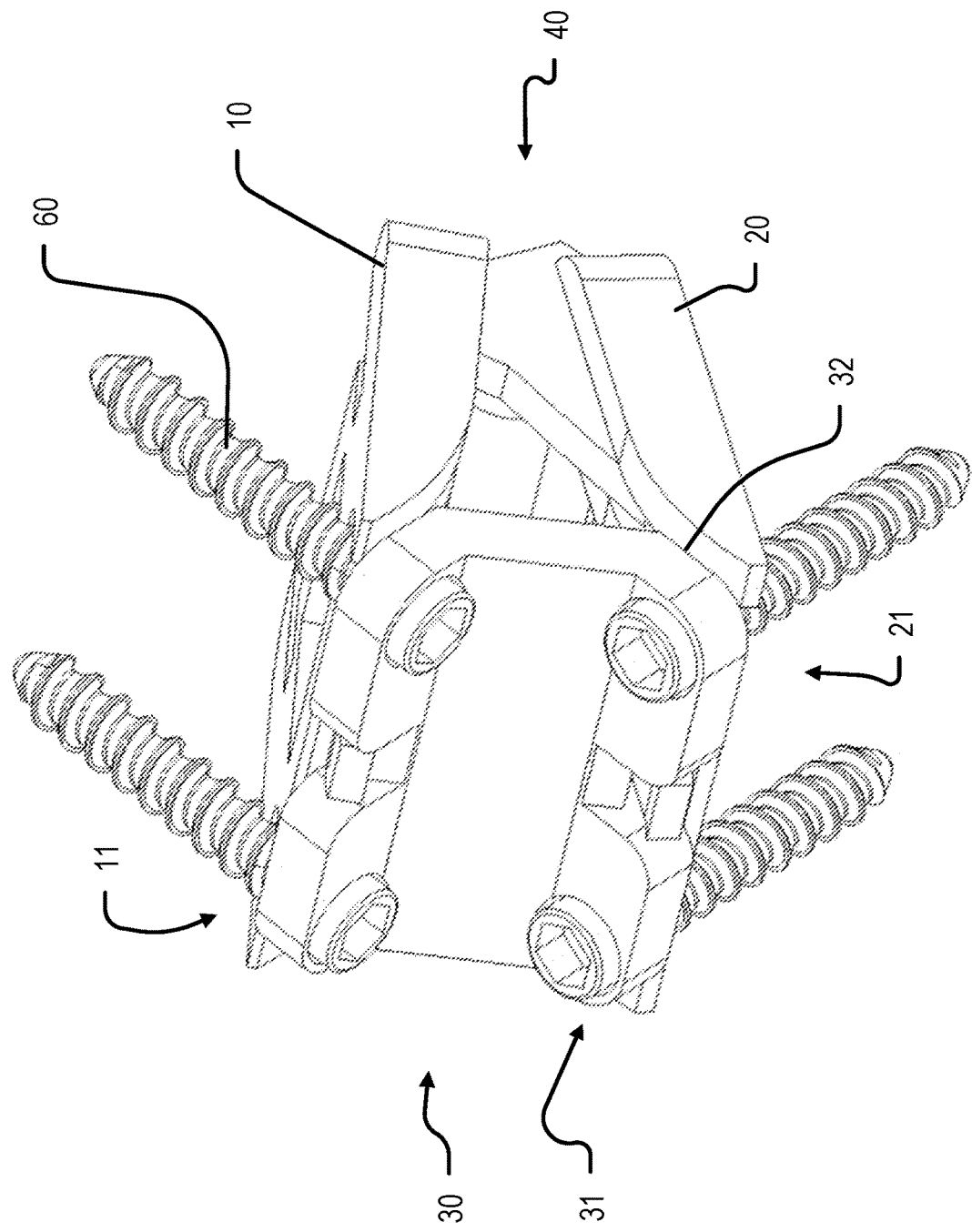
FIG. 14 is a perspective view showing an installation of a plurality of bone screws in a proximal plate.
Figure 15:
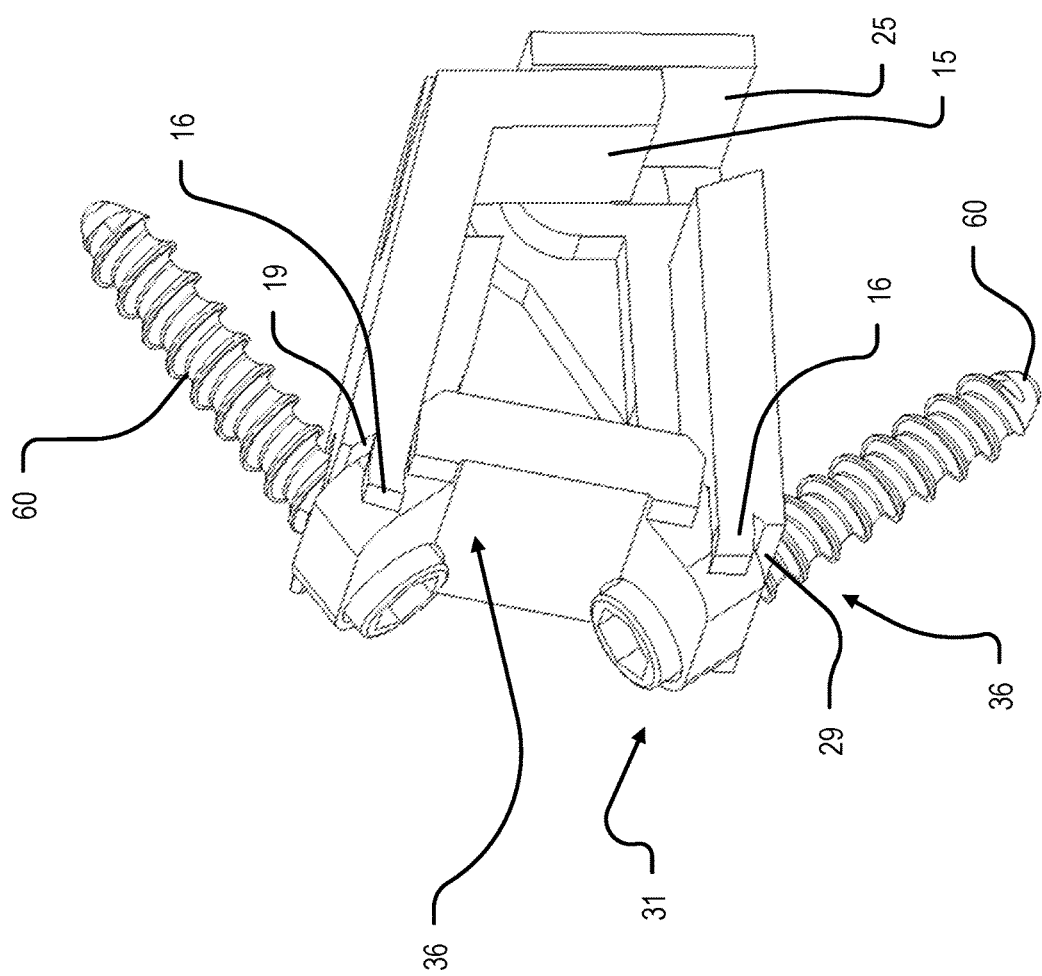
FIG. 15 is a sectioned perspective view of the embodiment of FIG. 14.
Figure 16:
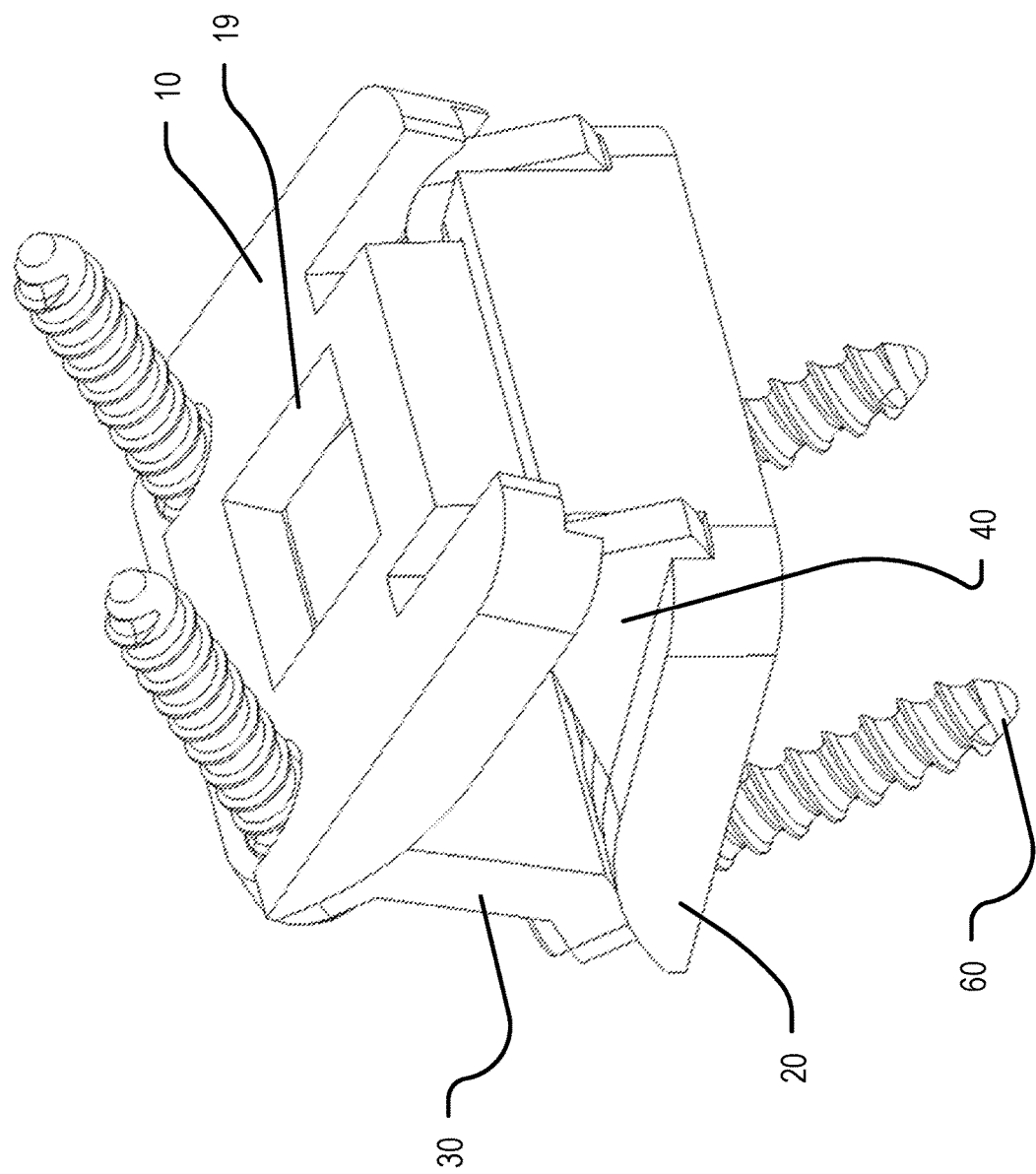
FIG. 16 is a rear perspective view of the embodiment of FIGS. 14 and 15.

FIGS. 13 and 14 are perspective views showing an installation of a bone screw 60 in a proximal plate 30. FIG. 15 is a sectioned perspective view of the embodiment of FIG. 14 and FIG. 16 is a rear perspective view of the embodiment of FIGS. 14 and 15. In the example embodiment, a plurality of bone screws 60 extend through bone screw apertures 31 of proximal plate 30 and over bone screw cutouts 11, 21 of the superior endplate 10 and inferior endplate 20, respectively. In some embodiments, bone screw cutouts 11, 21 may be a type of threaded aperture in which the bone screw 60 threadably engages with to lock implant 100 in a desired configuration. In the example embodiment, the bone screws 60 urge the proximal plate 30 into direct contact with the superior endplate 10 and inferior endplate 20, making it relatively difficult to overcome the curvature in protrusions 16 and 26 by grooves 36, thereby securing and/or locking a final configuration of the implant 100. For example, once the bone screws 60 are secured to an adjacent boney structure, such as a vertebrae, the relative position of the proximal plate 30 is fixed and the relative height and angle of inclination of implant 100 is also fixed.

Additionally, in some embodiments having the shims 40 extend in a proximal to distal direction, the distraction limitation features, such as lateral protrusions 14 and slots 24 extending laterally, and a proximal plate 30 anteriorly, a large central cavity between the interior surface of superior endplate 10 and the interior surface of inferior endplate 20 allows for graft placement. In various embodiments, the graft may also be contained by the distal walls 15, 25, shims 40 to keep it from migrating post op. In the example embodiment of FIG. 16, a graft window 19 is included of which a graft or bone growth promoting material may be placed pre-operatively and/or post-operatively thereby allowing bone ingrowth from the surrounding anatomy. In some embodiments, the superior endplate 10 and inferior endplate 20 may both include graft windows and in others only the superior endplate 10 may include a graft window 19. In various embodiments, and depending on angle of insertion, shims 40 may define the posterior height, proximal plate 30 may define the anterior height and any combination of appropriately sized shims 40 and proximal plate 30 may provide a surgeon with means to expand implant 100 to any desired angle and/or distraction. It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof

What is claimed is:

1. An expandable implant, comprising:
    a superior endplate including a first distal surface supporting a first protrusion extending in a first lateral direction and a second protrusion extending in a second lateral direction opposite the first lateral direction, the superior endplate having a third protrusion extending in a proximal direction, the superior endplate having a first track and a second track extending in a proximal-to-distal direction;
    an inferior endplate including a second distal surface supporting a first slot and a second slot, the inferior endplate having a fourth protrusion extending in a proximal direction, the inferior endplate having a third track and a fourth track extending in the proximal-to-distal direction;
    a proximal plate having a superior recess and an inferior recess disposed in a medial position of the proximal plate,
    a first shim disposed within the first track and the third track; and
    a second shim disposed within the second track and the fourth track,
    wherein the first protrusion is disposed within the first slot and the second protrusion is mated within the second slot.

2. The expandable implant of claim 1, wherein the proximal plate comprises an inclined superior bearing surface and an inclined inferior bearing surface.

3. The expandable implant of claim 2, wherein the superior endplate comprises a proximal engagement surface and the inferior endplate comprises a proximal engagement surface.

4. The expandable implant of claim 3, wherein the inclined superior bearing surface supports the proximal engagement surface of the superior endplate and the inclined inferior bearing surface supports the proximal engagement surface of the inferior endplate.

5. The expandable implant of claim 1, wherein the first track, the second track, the third track, and the fourth track each comprise, respectively, an arcuate socket.

6. The expandable implant of claim 5, wherein the first shim comprises a first bulbous distal end and the second shim comprises a second bulbous distal end.

7. The expandable implant of claim 6, wherein the first bulbous end is movable within the respective arcuate sockets of the first track and the third track and the second bulbous end is movable within the respective arcuate sockets of the second track and the fourth track.

8. The expandable implant of claim 7, wherein the first bulbous end is defined by a first height and the second bulbous end is defined by a second height that is substantially equal to the first height.

9. The expandable implant of claim 7, wherein the first bulbous end is defined by a first height and the second bulbous end is defined by a second height that is greater than the first height.

10. The expandable implant of claim 1, wherein the proximal plate includes at least one bone screw aperture.

11. The expandable implant of claim 10, further comprising at least one bone screw extending through the at least one bone screw aperture.

12. The expandable implant of claim 11, wherein the superior endplate comprises at least one bone screw relief and the inferior endplate comprises at least one bone screw relief.

13. The expandable implant of claim 1, wherein the first lateral protrusion and the second lateral protrusion each comprise, respectively, an arcuate surface.

14. The expandable implant of claim 13, wherein the first distal surface is positioned proximal with respect to the second distal surface.

15. The expandable implant of claim 14, wherein the first distal surface is inclined at an angle with respect to an outside surface of the superior endplate.

16. An expandable implant, comprising:
    a superior endplate and an inferior endplate hingedly coupled together, at least one of the superior endplate and the inferior endplate having at least one track extending in a proximal-to-distal direction on an interior surface thereof;
    a proximal plate having a superior engagement surface and an inferior engagement surface; and
    at least one shim disposed within the at least one track of the at least one of the superior endplate and the inferior endplate, the at least one shim defining an angle of inclination between the superior endplate and the inferior endplate;
    wherein the superior endplate is supported by the superior engagement surface and the inferior endplate is supported by the inferior engagement surface.

17. The expandable implant of claim 16, wherein: the superior endplate comprises a first protrusion extending from a proximal side of the superior endplate in the proximal-to-distal direction; and the inferior endplate comprises a second protrusion extending from a proximal side of the inferior endplate in the proximal-to-distal direction.

18. The expandable implant of claim 17, wherein
    the proximal plate comprises a first recess and a second recess, and
    the first protrusion is nested within the first recess and the second protrusion is nested within the second recess.

19. The expandable implant of claim 16, wherein: the superior endplate comprises a first lateral protrusion and a second lateral protrusion opposite the first lateral protrusion, the inferior endplate comprises a first slot and a second slot, the first and second slots having a size and shape that corresponds to the first lateral protrusion and the second lateral protrusion, and the first lateral protrusion is disposed within the first slot and the second lateral protrusion is disposed with the second slot.

20. The expandable implant of claim 16, wherein: the at least one track of the at least one of the superior endplate and the inferior endplate comprises an arcuate socket, and the at least one shim comprises a bulbous distal end and a tapered proximal end, the bulbous distal end being disposed within the arcuate socket.

* * * * *